US012630810B2

(12) United States Patent
Rissom et al.

(10) Patent No.: US 12,630,810 B2
(45) Date of Patent: May 19, 2026

(54) POLYPEPTIDE HAVING β-HEXOSAMINIDASE ACTIVITY, AND POLYNUCLEOTIDES CODING FOR THE SAME

(71) Applicant: Genzyme Corporation, Cambridge, MA (US)

(72) Inventors: Sebastian Rissom, Frankfurt am Main (DE); Ava Chattopadhyay, Frankfurt am Main (DE); Werner Dittrich, Frankfurt am Main (DE); Thomas Martin Wendrich, Frankfurt am Main (DE)

(73) Assignee: Genzyme Corporation, Cambridge, MA (US)

( * ) Notice: Subject to any disclaimer, the term of this patent is extended or adjusted under 35 U.S.C. 154(b) by 367 days.

(21) Appl. No.: 18/255,832

(22) PCT Filed: Dec. 2, 2021

(86) PCT No.: PCT/EP2021/084004
§ 371 (c)(1),
(2) Date: Jun. 2, 2023

(87) PCT Pub. No.: WO2022/117743
PCT Pub. Date: Jun. 9, 2022

(65) Prior Publication Data
US 2024/0110168 A1 Apr. 4, 2024

Related U.S. Application Data

(60) Provisional application No. 63/120,608, filed on Dec. 2, 2020.

(30) Foreign Application Priority Data

Dec. 11, 2020 (EP) .................................... 20213521

(51) Int. Cl.
*C12N 9/24* (2006.01)

(52) U.S. Cl.
CPC .... *C12N 9/2402* (2013.01); *C12Y 302/01052* (2013.01)

(58) Field of Classification Search
CPC ................................. C12N 9/24; C12N 9/2402
See application file for complete search history.

(56) References Cited

U.S. PATENT DOCUMENTS

| | | | |
|---|---|---|---|
| 8,299,318 B2 * | 10/2012 | Brover ................. | C07K 14/415 536/23.6 |
| 2004/0031072 A1 | 2/2004 | La Rosa et al. | |
| 2011/0083234 A1 * | 4/2011 | Nguyen ................... | A01H 5/10 800/278 |

FOREIGN PATENT DOCUMENTS

| | | |
|---|---|---|
| CN | 109971736 A | 7/2019 |

OTHER PUBLICATIONS

Swennen et al., "Secretion of active anti-Ras single-chain Fv antibody by the yeasts *Yarrowia lipolytica* and *Kluyveromyces lactis*," Microbiol. (2002) 148:41-50.
Akeboshi et al., "Production of Recombinant β-Hexosaminidase A, a Potential Enzyme for Replacement Therapy for Tay-Sachs and Sandhoff Diseases, in the Methylotrophic Yeast *Ogataea minuta*," Appl Environ Microbiol. (2007) 73(15):4805-12.
Al-Fattani and Douglas, "Biofilm matrix of Candida albicans and Candida tropicalis: chemical composition and role in drug resistance", J Med Microbiol. (2006) 55:999-1008.
Database NCBI GenPept [Online], "beta-hexosaminidase 1 [Glycine max]." (Aug. 31, 2018) https://www.ncbi.nlm.nih.gov/protein/XP_003552672.1 [Retrieved from NCBI accession No. XP_003552672.1 on Jun. 1, 2023].
Gers-Barlag et al., "β-N-Acetylhexosaminidase From Soybean," Phytochemistry. (1988) 27(12):3739-41.
Leonard et al., "Plant glycosidases acting on protein-linked oligosaccharides", Phytochemistry (2009) 70(3):318-24.
Li and Li, "Studies on the glycosidases of jack bean meal. 3. Crystallization and properties of beta-N-acetylhexosaminidase," J Biol Chem. (1970) 245(19):5153-60.
Slamova et al., "Sequencing, cloning and high-yield expression of a fungal β-N-acetylhexosaminidase in Pichia pastoris," Protein Expr Purif. (2012) 82(1):212-17.
Strasser et al., "Enzymatic Properties and Subcellular Localization of Arabidopsis β-N-Acetylhexosaminidases," Plant Physiol. (2008) 147(2):931.
DATABASE UniProt [Online] "RecName: Full=Beta-hexosaminidase {UniRule PIRNR: PIRNR001093 EnsemblPlants: KRH43642}." (Jan. 9, 2013) https://www.uniprot.org/uniprotkb/11KTU6/entry. [Retrieved from UniProt accession No. UNIPROT: 11KTU6 on Sep. 7, 2023].
DATABASE UniProt [Online] "RecName: Full=Beta-hexosaminidase {UniRule PIRNR: PIRNR001093 EnsemblPlants: KRH70518}." (Jun. 13, 2012) https://www.uniprot.org/uniprotkb/11JDS6/entry. [Retrieved from UniProt accession No. UNIPROT: 11JDS6 on Sep. 7, 2023].

* cited by examiner

*Primary Examiner* — Tekchand Saidha
(74) *Attorney, Agent, or Firm* — Steptoe LLP; Yi Han Dulkeith; Z. Ying Li

(57) ABSTRACT

The present invention relates to a method of producing a polypeptide having β-hexosaminidase activity, comprising the steps of a) providing a yeast cell comprising a polynucleotide encoding a polypeptide having β-hexosaminidase activity and having an amino acid sequence being at least 95% identical to the amino acid sequence shown in SEQ ID NO: 1, b) cultivating said yeast cell under conditions which allow for the production of the polypeptide, and c) obtaining the polypeptide produced in step b). The present invention further concerns a polynucleotide encoding a polypeptide having β-hexosaminidase activity and having an amino acid sequence being at least 95% identical to the amino acid sequence shown in SEQ ID NO: 1, as well as polypeptide encoded by said polynucleotide. Moreover, the present invention concerns a yeast cell comprising the polynucleotide of the present invention.

12 Claims, No Drawings

Specification includes a Sequence Listing.

1

POLYPEPTIDE HAVING β-HEXOSAMINIDASE ACTIVITY, AND POLYNUCLEOTIDES CODING FOR THE SAME

CROSS-REFERENCE TO RELATED APPLICATIONS

The present application is a national stage application under 35 U.S.C. § 371 of International Patent Application No. PCT/EP2021/084004, filed Dec. 2, 2021, which claims priority to EP patent application No. 20213521.6, filed Dec. 11, 2020 and U.S. Provisional Patent Application No. 63/120,608, filed Dec. 2, 2020. The contents of the aforementioned priority applications are incorporated herein by reference in their entirety.

SEQUENCE LISTING

The instant application contains a Sequence Listing that has been submitted electronically in ASCII format in PCT/EP2021/084004 and is hereby incorporated by reference in its entirety. The ASCII copy, named SAN16068PC Sequence listing.txt, is 18,620 bytes in size.

FIELD OF THE INVENTION

The present invention relates to a method of producing a polypeptide having β-hexosaminidase activity, comprising the steps of a) providing a yeast cell comprising a polynucleotide encoding a polypeptide having β-hexosaminidase activity and having an amino acid sequence being at least 95% identical to the amino acid sequence shown in SEQ ID NO: 1 or 16, b) cultivating said yeast cell under conditions which allow for the production of the polypeptide, and c) obtaining the polypeptide produced in step b). The present invention further concerns a polynucleotide encoding a polypeptide having β-hexosaminidase activity and having an amino acid sequence being at least 95% identical to the amino acid sequence shown in SEQ ID NO: 1, as well as polypeptide encoded by said polynucleotide. Moreover, the present invention concerns a yeast cell and a vector comprising the polynucleotide of the present invention.

BACKGROUND

β-hexosaminidase (EC 3.2.1.52, abbreviated "b-Hex" herein) is an enzyme that catalyzes the hydrolysis of terminal nonreducing N-acetylhexosamine residues in N-acetyl-beta-hexosaminides. The enzyme is frequently also referred to as N-acetyl-beta-glucosaminidase. N-Acetylglucosides and N-acetylgalactosides are substrates.

Three major forms of the β-hexosaminidase are found in mammals: a trimer consisting of one alpha chain, one beta-A chain, and one beta-B chain (Form A), a tetramer consisting of two beta-A chains and two beta-B chains (Form B), and a homodimer of two alpha chains (Form S). It is known that some genetic disorders such as Tay-Sachs disease and Sandhoff's disease result from mutations in the human b-Hex gene.

Glycosidases have been used as tools in glycobiology research for decades, and their role in glycoprotein maturation has been studied (as reviewed by Léonard R, Strasser R, Altmann F. Plant glycosidases acting on protein-linked oligosaccharides. Phytochemistry. 2009 February; 70(3): 318-24. doi: 10.1016/j.phytochem. 2009.01.006. Epub 2009 Feb. 4. PMID: 19200565).

A β-hexosaminidase enzyme preparation currently used for glycan modification is extracted from its natural source Jack Beans (*Canavalia ensiformis*). The basic description of the enzyme and of the base of the current extraction process can be found in Li et al. (J. Biol. Chem. 1970 245: 5153-5160). The enzyme has been used, for example, to study enzymatic detachment of biofilms (J Med Microbiol. 2006 August; 55 (Pt 8):999-1008).

This current extraction process however has several disadvantages:

Jack Bean being a plant grown on fields has the disadvantages of such natural systems: High level of irreproducibility due to weather, soil, etc. conditions (see Li (1970)). As consequence new secondary metabolites could arise, which then introduced into the production process might finally contaminate the drug substance with incalculable effects on the patient health. Use of agrochemicals to maintain fertility and to avoid damage to plants can lead to residues within the product. Presence of fungi or other microbial contaminants in the soil, on the plants or on the beans during culture or storage can lead to the contamination of the product by toxins such as aflatoxins that can have a very toxic effect even in small amounts.

B-Hex is not a very abundant protein in Jack Beans as the plant does not need high quantities of this enzyme under natural conditions. It is present in only very small activities of about 1 U/g of bean material and thus needs to be extracted and subsequently separated and purified from a large number and quantity of contaminating proteins. This difficult procedure results in a high need of plant material to be used as substrate and makes this process very costly.

Except for the few data described for b-Hex described in early 1970s (see Li et al., cited above), there is not a lot known about this enzyme. Notably, there is no protein or DNA sequence publicly available. No detailed structural characterization of the enzyme has been made.

Gers-Barlag et al. describe the isolation of the β-hexosaminidase from soybean (Phytochemistry, Volume 27, Issue 12, 1988, Pages 3739-3741). US 2004/0031072 discloses the sequence of the β-hexosaminidase from soybean (as SEQ ID NO: 162900). Soybean β-hexosaminidase sequences can be also assessed via UniProt (see accession number I1KTU6 or I1JDS6 which corresponds to NCBI Reference Sequence: XP 003518662.1).

CN 109 971 736 describes the identification of an hexosaminidase enzyme from strawberry.

Slámová et al. describe the cloning and high-yield expression of a fungal b-N-acetylhexosaminidase in *Pichia pastoris* (Protein Expr Purif. 2012 March; 82(1):212-7. doi: 10.1016/j.pep.2012.01.004. Epub 2012 Jan. 11).

Strasser describes the heterologous expression of three putative b-Hex sequences present in the *Arabidopsis* (*Arabidopsis thaliana*) genome (Strasser et al., Plant Physiol. 2008 June; 147(2):931). The authors used a *Spodoptera frugiperda* Sf21 insect cell system for expression. The authors also showed that these plant enzymes have only very limited homology of around 30% with the well-studied human b-Hex enzymes HexA and HexB. It is thus not astonishing that the microbial expression in the methylotrophic yeast Ogataea minuta described in Akeboshi et al. for the human HexA would not be transposable to plant enzymes (Akeboshi et al., Appl Environ Microbiol. 2007 August; 73(15):4805-12). This is especially true as the authors describe two major differences between the recombinant HexA from *O. minuta* and native HexA from human lysosomes corresponding to different post-translational processing between both organisms.

SUMMARY OF THE PRESENT INVENTION

In the context of the studies underlying the present application, a detailed analysis of the b-Hex enzyme isolated from Jack Bean (*Canavalia ensiformis*) was carried out in order to determine as much of the protein sequence as possible. This was done by applying a combination of protease digestion, Edman sequencing and LC-MS/MS analyses, and led to about 40% sequence coverage of the protein (Example 2). With this result, it was possible to confirm by data base search that effectively no match to the found sequence was available. The closest sequences found belong to b-Hex proteins from Soy Bean (*Glycine max*). Further, the full length cDNA sequence coding for the Jack Bean b-Hex enzyme was determined (Example 3). The alignment with sequences available in databases revealed no known sequence to match the one determined, thus the detected β-hexosaminidase polypeptide seems to be not known to the public domain.

Advantageously, it was possible to express the β-hexosaminidase polypeptide in a microbial system, namely in *Komagataella phaffii* (sometimes also referred to as *Pichia pastoris*). Supernatants of cultures containing the generated *Komagataella phaffii* strains showed a significant amount of b-Hex activity (Example 4). It was shown that more than 100 U/mL of culture can be achieved. Additionally, the culture supernatant did not contain major amounts of contaminating proteins. This allows a straight-forward reproducible protein purification process.

The *Klyveromyces lactis* expression system described by Swennen (2002) was chosen as a second example. The recombinant expression of b-Hex was also successful for this yeast system as biologically active b-Hex was found in the respective yeast cultures.

It was shown that the b-Hex enzyme from Jack Bean is not present in a single polypeptide chain as it would be expected by translating the found DNA sequence into a protein sequence. It was rather found that there are two polypeptide chains associated with each other without being covalently linked. Dissociation of the two chains led to a complete loss of activity. Therefore, it was surprising that the recombinant microbial expression yielded active enzyme, since it was not expected that the identified b-Hex enzyme would reproduce such split into two chains and in the same time ensure that these two chains are associated in the correct structure.

Accordingly, the present invention relates to a method of producing a polypeptide having β-hexosaminidase activity, comprising the steps of a) providing a host cell comprising a polynucleotide encoding a polypeptide having β-hexosaminidase activity and having an amino acid sequence being at least 85% identical to the amino acid sequence shown in SEQ ID NO: 1 or 16, b) cultivating said host cell under conditions which allow for the production of the polypeptide, and c) obtaining the polypeptide produced in step b).

The present invention further relates to a polynucleotide encoding a polypeptide having β-hexosaminidase activity and having an amino acid sequence being at least 85% identical to the amino acid sequence shown in SEQ ID NO: 1 or 16.

Further encompassed by the present invention is an isolated polypeptide encoded by the polynucleotide of the present invention.

Moreover, the present invention is directed to a vector comprising the polynucleotide of the present invention. In some embodiments, the vector is an expression vector.

The present invention further pertains to a host cell comprising the polynucleotide of the present invention, the polypeptide of the present invention and/or the vector of the present invention.

In some embodiments, the host cell of the present invention is a yeast cell or animal cell. For example, the host cell may be a yeast cell belonging to the family of Saccharomycetaceae, such as a *Komagataella phaffii* cell.

In some embodiments, the polypeptide of the present invention has an amino acid sequence which is at least 90% identical, such as 95% or 98% identical, to the amino acid sequence shown in SEQ ID NO: 1 or 16. In some embodiments, the polypeptide comprises an amino acid sequence as shown in SEQ ID NO: 1 or 16.

In some embodiments, the polynucleotide of the present invention comprises a nucleic acid sequence as shown in SEQ ID NO: 2. In some embodiments, the polynucleotide of the present invention comprises a nucleic acid sequence as shown in SEQ ID NO: 17.

In some embodiments, the polynucleotide of the present invention is operably linked to a heterologous promoter.

In some embodiments, the polynucleotide of the present invention is codon optimized for the host cell, such as a yeast cell.

DETAILED DESCRIPTION OF THE PRESENT INVENTION

Definitions

As set forth above, the present invention relates to a method of producing a polypeptide having β-hexosaminidase activity, comprising the steps of a) providing a host cell comprising a polynucleotide encoding a polypeptide having β-hexosaminidase activity and having an amino acid sequence being at least 85% identical to the amino acid sequence shown in SEQ ID NO: 1 or 16, b) cultivating said host cell under conditions which allow for the production of the polypeptide, and c) obtaining the polypeptide produced in step b).

In step a) of the method of the present invention, a host cell shall be provided comprising a polynucleotide encoding a polypeptide having β-hexosaminidase activity.

The term "polynucleotide" as used herein refers to a linear or circular nucleic acid molecule. It encompasses DNA as well as RNA molecules. The polynucleotide shall be provided either as an isolated polynucleotide (i.e. isolated from its natural context) or in genetically modified form. The polynucleotide as set forth herein is characterized in that it shall encode a polypeptide as referred to above, i.e. a polypeptide having β-hexosaminidase activity.

The terms "polypeptide" and "protein" are used interchangeably herein and refer to amino acids in a polymeric form linked together by peptide bonds.

The polypeptide produced by the method of the present invention shall have β-hexosaminidase activity.

As used herein, β-hexosaminidase (EC 3.2.1.52) typically refers to an enzyme being capable of catalysing the hydrolysis of terminal nonreducing N-acetylhexosamine residues in N-acetyl-beta-hexosaminides. For example, N-acetylglucosides and N-acetylgalactosides are substrates. Assays for assessing whether a polypeptide has β-hexosaminidase activity are known in the art and described, for example, in Li & Li (1970) J Biol Chem 245 5153: They show b-hexosaminidase activity for following substrates: p-nitrophenyl β-2-acetamido-2-deoxy-p-glucopyranoside and p-nitrophenyl β-2-acetamido-2-deoxy-p-galactopyranoside. Synonyms are β-hexosaminidase, β-(1-2,3,4,6) Hexosaminidase; β-acetylamino-deoxyhexosidase, N-acetyl-β-D-hexosaminidase; N-acetyl-β-hexosaminidase; β-acetylhexosaminidinase, β-D-N-acetylhexosaminidase; β-N-acetyl-D-hexosaminidase, β-N-acetylglucosaminidase, N-acetylhexosaminidase and β-D-hexosaminidase.

In some embodiments, the polypeptide having β-hexosaminidase activity forms a homodimer.

In some embodiments, the polypeptide having β-hexosaminidase activity is expressed from a heterologous polynucleotide, i.e. from a polynucleotide which has been either transiently, e.g., by using an expression vector, or stably introduced into the host cell. The term "heterologous" as used herein means that the polynucleotide does not occur naturally in the host cell. The term, thus, encompasses modified or unmodified polynucleotides which are derived from different organisms or modified polynucleotides derived from the host cell. It is to be understood that the heterologous polynucleotide may either comprise expression control sequences which allow for expression in the host cell or sequences which allow for integration of the heterologous polynucleotide at a locus in the genome of the host cell where the expression of the heterologous polynucleotide will be governed by endogenous expression control sequences of the host cell. By introducing the heterologous polynucleotide, a transgenic host cell is generated.

The introduction of the polypeptide having β-hexosaminidase activity may be achieved by introducing heterologous polynucleotides encoding the said polypeptide into the host cell. The term "introduction" or "transformation" as referred to herein encompasses the transfer of a polynucleotide as described herein into a host cell, irrespective of the method used for transfer. This includes transient introduction in expression vectors or stable integration into the genome of the host cell. In some embodiments, the polynucleotide is stably introduced into the genome of the host cell.

Thus, step a) of the method of the present invention may comprise the steps of:

a1) introducing the polynucleotide encoding the polypeptide having β-hexosaminidase activity into the host cell; and a2) expressing said polypeptide from the said polynucleotide.

The term "expression" or "gene expression" means the transcription of a specific gene or specific genes or specific genetic construct. The term "expression" or "gene expression" in particular means the transcription of a gene or genes or genetic construct into structural mRNA with subsequent translation of the latter into a polypeptide as referred herein. The process includes transcription of DNA and processing of the resulting mRNA product.

As set forth above, the polypeptide encoded by the polynucleotide of the present invention shall have β-hexosaminidase activity. In addition, it shall have an amino acid sequence being at least 85%, 90%, 91%, 92%, 93%, 94%, 95%, 96%, 97%, 98%, 99% or 100% identical to the amino acid sequence shown in SEQ ID NO: 1 or 16.

In some embodiments, the polypeptide having β-hexosaminidase activity has an amino acid sequence which is at least 95% identical, such as at least 98% identical to the amino acid sequence shown in SEQ ID NO: 1 or 16.

In some embodiments, the polypeptide having β-hexosaminidase activity comprises an amino acid sequence as shown in SEQ ID NO: 16.

SEQ ID NO: 16 is the amino acid sequence of the Jack Bean (Canavalia ensiformis) β-hexosaminidase identified in the studies underlying the present invention. The sequence is as follows:

```
MFLCIPRWFS SPLLILFVIY CALFAPQAAS ATLKSIIEPT

ESLTYLWPLP ADFTSGDETL SVDPALTLSV AGNGGGSSIL

RDAFDRYRGI IFKHSSVGFS LIRKLRERLV SVSAYDIATL

KITVHSDNEE LQLGVDETYT LLVPKAKDSY VAGEVTIEAN

TVYGALRGLE TFSQLCSFDY SDKTIKIYKA PWSIQDKPRF

SYRGLLLDTS RHYLPINVIK QIIESMSYAK LNVLHWHIID

EESFPLEVPT YPNLWKGSYT KWERYTVEDA YEIVNFAKMR

GINVMAEVDV PGHAESWGAG YPNLWPSPSC REPLDVSKNF

TFDVISGILT DIRKIFPFEL FHLGGDEVNT DCWTSTSHVK

EWLSTQNMTA KDAYEYFVLK AQEIAVSKNW SPVNWEETFN

TFPAKLHKKT VVHNWLGPGV CPKVVAKGFR CIFSNQGVWY

LDHLDVPWDE VYTAEPLEGI EKSSEQELVI GGEVCMWGET

ADTSNVQQTI WPRAAAAAER LWSQRDSTNI TVTALPRLQN

FRCLLNKRGV AAAPVKNYYA RRAPSGPGSC YEQ
```

The sequence of a potential leaded sequence (aa 1 to 30) is underlined. In the studies underlying the present invention, the polypeptide was expressed without the leader sequence. SEQ ID NO: 1 is the amino acid sequence of the Jack Bean (Canavalia ensiformis) β-hexosaminidase without the leader sequence. Accordingly, SEQ ID NO: 1 comprises aa 31 to 553 of SEQ ID NO: 16. SEQ ID NO: 1 is as follows:

```
ATLKSIIEPT ESLTYLWPLP ADFTSGDETL SVDPALTLSV

AGNGGGSSIL RDAFDRYRGI IFKHSSVGFS LIRKLRERLV

SVSAYDIATL KITVHSDNEE LQLGVDETYT LLVPKAKDSY

VAGEVTIEAN TVYGALRGLE TFSQLCSFDY SDKTIKIYKA

PWSIQDKPRF SYRGLLLDTS RHYLPINVIK QIIESMSYAK

LNVLHWHIID EESFPLEVPT YPNLWKGSYT KWERYTVEDA

YEIVNFAKMR GINVMAEVDV PGHAESWGAG YPNLWPSPSC

REPLDVSKNF TFDVISGILT DIRKIFPFEL FHLGGDEVNT

DCWTSTSHVK EWLSTQNMTA KDAYEYFVLK AQEIAVSKNW

SPVNWEETFN TFPAKLHKKT VVHNWLGPGV CPKVVAKGFR

CIFSNQGVWY LDHLDVPWDE VYTAEPLEGI EKSSEQELVI

GGEVCMWGET ADTSNVQQTI WPRAAAAAER LWSQRDSTNI

TVTALPRLQN FRCLLNKRGV AAAPVKNYYA RRAPSGPGSC YEQ
```

In an embodiment, SEQ ID NO: 1 additionally comprises a methionine residue (M) at the N-terminal end.

In an embodiment, the above polypeptide is encoded by a polynucleotide comprising a nucleic acid sequence as shown in SEQ ID NO: 2:

gctactttgaagtccatcatcgagccaactgagtccttgacttacttgtg gccattgccagctgacttcacttctggtgacgaaacttttgtctgttgacc cagctttgactttgtccgttgctggtaatggtggtggttcctccattttg agagatgctttcgacagatacagaggtattatcttcaagcactcctccgt tggattctctttgatcagaaagttgagagagagattggtttccgtttccg cttacgacattgctactttgaagatcactgttcactccgacaacgaagag ttgcagttgggtgttgacgagacttacactttgttggttccaaaggctaa ggactcctacgttgctggtgaggttactatcgaggctaacactgtttacg gtgctttgagaggtttggagactttctcccagttgtgttccttcgactac tctgacaagactatcaagatttacaaggctccttggtccatccaggacaa gccaagattttcctacagaggtttgttgttggacacttccagacactact tgccaatcaacgttatcaagcagatcatcgagtccatgtcctacgctaag ttgaacgttttgcactggcacatcatcgacgaagagtctttcccattgga ggttccaacttacccaaacttgtggaagggttcctacactaagtgggaga gatacactgttgaggacgcttacgagatcgttaacttcgctaagatgaga ggtattaacgttatggctgaggttgacgttccaggtcatgctgaatcttg gggtgctggttatccaaatttgtggccatctccatcctgtagagagccat tggacgtttccaagaacttcactttcgacgttatctccggaatcttgact gacatcagaaagatattcccattcgagttgttccacttgggaggtgacga ggttaatactgactgttggacttccacttcccacgttaaggaatggttgt ccactcagaacatgactgctaaggatgcttacgaatacttcgttttgaag -continued gctcaagagatcgctgtttctaagaactggtcccctgttaactgggaaga gactttcaacactttcccagctaagttgcacaagaaaactgttgttcaca actggttgggtccaggtgtttgtccaaaggttgttgctaagggtttcaga tgtatcttctccaaccagggtgtttggtacttggaccacttggatgttcc ttgggacgaggtttacactgctgaaccattggaaggtatcgagaagtcct ctgagcaagagttggttatcggtggtgaagtttgtatgtggggtgagact gctgacacttctaacgttcagcagactatctggccaagagccgcagctgc tgctgaaagattgtggtcccaaagagactccactaacatcactgttactg ctttgccaagattgcagaacttcagatgtttgttgaacaagagaggtgtt gctgctgctccagttaagaactactacgctagaagagcccccatccggtcc aggttcttgttacgaacaa SEQ ID NO: 2 may further comprise a start codon (ATG) at the 5' end and one or more stop codons at the 3' end.

Upon expression of the polypeptide in the host cell, the polypeptide may be further processed. For example, the polypeptide may be processed into two subunits, wherein the first subunit comprises amino acids 35 to 100 of SEQ ID NO: 16 and the second subunit comprises amino acids 110 to 553 of SEQ ID NO: 16. The start and end of the first subunit and start of second subunit may vary slightly. For example, subunits comprising amino acids 34 to 101 were also detected.

Further, the polypeptide may be hexosylated and/or glycosylated. For example, the first subunit may be hexosylated.

In one embodiment, the polypeptide having a sequence as shown in SEQ ID NO: 16 is encoded by a polynucleotide having a sequence shown in SEQ ID NO: 17. The sequence is as follows:

```
   1 ATGTTTCTGT GCATACCCAG ATGGTTCTCT TCACCTCTTC TCATTCTCTT TGTCATTTAC

61 TGTGCCCTCT TTGCTCCTCA AGCTGCTTCT GCCACACTCA AATCTATCAT TGAACCCACT

121 GAGTCCCTCA CATACCTTTG GCCCCTCCCC GCAGACTTCA CTTCAGGCGA TGAAACTCTT

181 TCCGTTGACC CTGCACTTAC CCTCTCTGTC GCCGGCAACG GTGGTGGCTC TTCCATTCTC

241 AGAGATGCAT TTGACCGATA CAGAGGAATC ATATTCAAGC ACAGCAGTGT TGGGGTTCAGT

301 CTCATAAGAA AGTTAAGGGA AAGATTGGTG TCTGTTTCTG CCTATGACAT TGCGACATTG

361 AAGATCACTG TCCATTCAGA TAACGAGGAG CTTCAACTTG GAGTGGATGA AACCTATACC

421 TTGCTGGTTC CCAAAGCCAA GGACTCTTAT GTTGCTGGGG AAGTCACAAT TGAGGCAAAC

481 ACTGTTTATG GTGCATTGCG CGGATTAGAG ACATTCAGCC AGTTGTGTTC TTTCGATTAT

541 TCGGATAAAA CAATAAAAAT ATACAAGGCA CCTTGGTCCA TCCAAGATAA ACCTAGATTT

601 TCCTATCGTG GGCTTTTGTT GGACACATCG AGGCACTATT TACCAATTAA CGTAATTAAG

661 CAGATTATTG AATCTATGTC CTATGCTAAA CTTAATGTTC TACATTGGCA CATCATAGAC

721 GAGGAGTCAT TTCCTCTTGA GGTACCTACA TATCCAAACT TGTGGAAAGG TTCATATACA

781 AAGTGGGAAC GTTACACGGT AGAAGACGCA TATGAAATTG TCAACTTCGC CAAAATGAGA

841 GGCATAAATG TGATGGCAGA AGTGGATGTT CCTGGTCATG CAGAATCATG GGGTGCTGGA

901 TATCCCAATC TTTGGCCGTC ACCTTCCTGT AGGGAGCCAC TGGATGTTTC AAAGAATTTT

961 ACTTTTGATG TCATTTCTGG TATCCTGACA GATATAAGAA AGATTTTCCC GTTTGAGCTA

1021 TTTCACTTGG GTGGTGATGA AGTTAATACA GATTGCTGGA CCAGTACTTC TCATGTGAAG
```

-continued

```
1081 GAATGGCTTT CGACTCAAAA CATGACTGCT AAAGATGCCT ATGAATATTT TGTACTGAAG

1141 GCCCAAGAGA TAGCTGTTTC AAAAAATTGG AGTCCGGTGA ACTGGGAAGA AACCTTCAAT

1201 ACATTTCCAG CAAAGCTCCA TAAGAAAACT GTGGTGCATA ACTGGTTGGG CCCTGGGGTT

1261 TGTCCAAAGG TTGTTGCAAA AGGTTTCAGG TGCATTTTCA GTAATCAGGG TGTCTGGTAT

1321 CTTGACCATC TGGATGTACC TTGGGATGAG GTCTATACTG CTGAGCCACT AGAAGGAATA

1381 GAAAAATCTT CTGAACAAGA GCTTGTAATT GGAGGAGAAG TTTGCATGTG GGGTGAGACA

1441 GCTGATACAT CCAATGTTCA GCAAACAATA TGGCCTAGAG CTGCTGCAGC TGCAGAACGC

1501 TTATGGAGTC AGAGAGATTC TACAAATATT ACTGTAACTG CGTTGCCCCG GTTACAAAAC

1561 TTCAGATGTC TATTGAATAA ACGTGGAGTT GCAGCTGCTC CTGTGAAAAA TTATTATGCT

1621 AGAAGGGCTC CTAGTGGTCC AGGCTCATGT TATGAGCAAT AA
```

In one embodiment, the polynucleotide encoding a polypeptide having β-hexosaminidase activity is codon optimized for the host cell, such as for a human cell. For example, the polynucleotide may comprise a sequence shown in SEQ ID NO: 18:

```
   1 GCCACACTGA AGTCCATCAT CGAGCCCACC GAGAGCCTGA CCTACCTGTG GCCTCTGCCC

61 GCCGATTTCA CCAGCGGCGA CGAGACACTG TCCGTGGATC CTGCCCTGAC ACTGAGCGTG

121 GCCGGAAATG GCGGCGGAAG CAGCATCCTG AGAGATGCCT TCGACCGGTA CAGAGGCATC

181 ATCTTCAAGC ACAGCAGCGT GGGCTTCAGC CTGATCCGGA AGCTGCGCGA GAGACTGGTG

241 TCCGTGTCCG CCTACGATAT CGCCACCCTG AAGATCACCG TGCACTCCGA CAACGAGGAA

301 CTGCAGCTGG GCGTGGACGA GACATACACC CTGCTGGTGC CCAAGGCCAA GGACAGCTAT

361 GTGGCCGGCG AAGTGACCAT CGAGGCCAAC ACAGTGTACG GCGCCCTGAG AGGCCTGGAA

421 ACCTTCAGCC AGCTGTGCAG CTTCGACTAC AGCGACAAGA CCATCAAGAT CTACAAGGCC

481 CCTTGGAGCA TCCAGGACAA GCCCCGGTTC AGCTACAGAG GCCTGCTGCT GGACACCAGC

541 AGACACTACC TGCCCATCAA CGTGATCAAG CAGATCATCG AGAGCATGAG CTACGCCAAG

601 CTGAACGTGC TGCACTGGCA CATCATCGAC GAGGAATCCT TCCCACTGGA AGTGCCCACC

661 TACCCCAACC TGTGGAAGGG CAGCTACACC AAGTGGGAGC GGTACACCGT GGAAGATGCC

721 TACGAGATCG TGAACTTCGC CAAGATGCGG GGCATCAATG TGATGGCCGA GGTGGACGTG

781 CCAGGCCACG CTGAATCTTG GGGAGCCGGC TACCCTAATC TGTGGCCCAG CCCCAGCTGT

841 CGCGAACCCC TGGACGTGTC CAAGAACTTC ACCTTCGACG TGATCAGCGG CATCCTGACC

901 GATATCAGAA AGATCTTCCC ATTCGAGCTG TTCCACCTGG GAGGCGACGA AGTGAACACC

961 GACTGCTGGA CCAGCACCAG CCACGTGAAA GAGTGGCTGA GCACCCAGAA CATGACCGCC

1021 AAGGACGCCT ACGAGTACTT CGTGCTGAAG GCCCAGGAAA TCGCCGTGTC TAAGAATTGG

1081 AGCCCCGTGA ACTGGGAGGA AACCTTTAAC ACCTTCCCTG CCAAACTGCA CAAGAAAACC

1141 GTGGTGCACA ATTGGCTGGG CCCTGGCGTG TGCCCTAAGG TGGTGGCCAA GGGCTTCCGC

1201 TGCATATTCA GCAACCAGGG CGTGTGGTAT CTGGACCACC TGGATGTGCC CTGGGACGAG

1261 GTGTACACAG CCGAGCCTCT GGAAGGCATC GAGAAGTCCT CCGAGCAGGA ACTCGTGATC

1321 GGCGGAGAAG TGTGCATGTG GGGCGAGACA GCCGACACCT CCAACGTGCA GCAGACCATC

1381 TGGCCTAGAG CCGCCGCTGC CGCTGAAAGA CTGTGGTCCC AGAGAGACAG CACCAACATC
```

```
1441 ACCGTGACCG CCCTGCCCCG GCTGCAGAAC TTTAGATGCC TGCTGAACAA GCGGGGCGTG

1501 GCCGCTGCCC CCGTGAAGAA TTACTATGCC AGAAGGGCCC CCAGCGGCCC TGGCAGCTGT

1561 TATGAACAGT GA
```

The polynucleotide comprising a sequence shown in SEQ ID NO: 18 encodes a polypeptide having β-hexosaminidase activity, wherein the polypeptide has a sequence as shown in SEQ ID NO: 1.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity. In some embodiments, standard parameters are applied for determining the degree of sequence identity of two sequences. For example, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. In some embodiments, the degree of sequence identity is determined over the entire length of the sequences. Given that two sequences have been identified for comparison, GAP and BESTFIT are preferably employed to determine their optimal alignment and, thus, the degree of identity. Preferably, the default values of 5.00 for gap weight and 0.30 for gap weight length are used. In an embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice, P., Longden, I., and Bleasby, A., Trends in Genetics 16(6), 276-277, 2000), a BLOSUM62 scoring matrix, and a gap opening penalty of 10 and a gap extension penalty of 0.5. A non-limiting example of parameters to be used for aligning two amino acid sequences using the needle program are the default parameters, including the EBLOSUM62 scoring matrix, a gap opening penalty of 10 and a gap extension penalty of 0.5.

The polynucleotide as referred to herein may either essentially consist of the aforementioned nucleic acid sequences or comprise the aforementioned nucleic acid sequences. Thus, they may contain further nucleic acid sequences as well.

In some embodiments, the polynucleotide encoding the polypeptide having β-hexosaminidase activity is operably linked to a promoter, such as a heterologous promoter. Typically, a promoter comprises regulatory elements which mediate the expression of a coding sequence segment in the host cell.

In one embodiment, the promoter is a constitutive promoter. In one alternative embodiment, the promoter is an inducible promoter.

A "promoter" or "promoter sequence" is a nucleotide sequence located upstream of a gene on the same strand as the gene that enables that gene's transcription. Promoter is followed by the transcription start site of the gene. A promoter is recognized by RNA polymerase (together with any required transcription factors), which initiates transcription. A functional fragment or functional variant of a promoter is a nucleotide sequence which is recognizable by RNA polymerase, and capable of initiating transcription.

An "active promoter fragment", "active promoter variant", "functional promoter fragment" or "functional promoter variant" describes a fragment or variant of the nucleotide sequences of a promoter, which still has promoter activity.

A promoter can be an "inducer-dependent promoter" or an "inducer-independent promoter" comprising constitutive promoters or promoters which are under the control of other cellular regulating factors.

The person skilled in the art is capable to select suitable promoters for expressing the polypeptide of interest. For example, the polynucleotide encoding the polypeptide of interest is, typically, operably linked to an "inducer-dependent promoter" or an "inducer-independent promoter". Further, the polynucleotide encoding the polypeptide having β-hexosaminidase activity is, typically, operably linked to an "inducer-independent promoter", such as a constitutive promoter.

An "inducer dependent promoter" is understood herein as a promoter that is increased in its activity to enable transcription of the gene to which the promoter is operably linked upon addition of an "inducer molecule" to the fermentation medium. Thus, for an inducer-dependent promoter, the presence of the inducer molecule triggers via signal transduction an increase in expression of the gene operably linked to the promoter.

In an embodiment, the promoter is a CMV promoter. For example, a CMV may be used when expressing the polypeptide having β-hexosaminidase activity in a mammalian host cell, such as a HEK-293 host cell.

In another embodiment, the promoter is a Tac promoter. For example, the Tac promoter may be used when expressing the polypeptide having β-hexosaminidase activity in a yeast host cell, such as a yeast cell disclosed herein below. The Tac-Promoter (abbreviated as Ptac), is a synthetically produced DNA promoter, produced from the combination of promoters from the trp and lac operons. It is commonly used for protein production.

In an embodiment, the promoter is the promoter of a polynucleotide encoding for an alcohol oxidase, such as a promoter from a yeast AOX1 (Alcohol Oxidase 1).

The term "operably linked", typically refers to a functional linkage between the promoter sequence and the gene of interest (i.e. the polynucleotide encoding a polypeptide having β-hexosaminidase activity), such that the promoter sequence is able to initiate transcription of the gene of interest.

Further, the polynucleotide as referred to herein may be operably linked to a terminator. The term "terminator" typically encompasses a control sequence which is a DNA sequence at the end of a transcriptional unit which signals 3' processing and polyadenylation of a primary transcript and termination of transcription.

The polynucleotide as referred to herein may be further operably linked to a polynucleotide which encodes for a secretion leader, i.e. a sequence which allows for secretion of the 8-hexosaminidase of the invention into the cultivation medium.

The host cell provided in step a) of the method of the present invention may be any host cell deemed appropriate. For example, the host selected from the group consisting of bacterial cells, such as an *E. coli* cell, a yeast cell, an algal cell, or a plant cell. The term "host cell" further includes animal cells, such as non-human animal cells.

In some embodiments, the host cell is a eukaryotic host cell.

In some embodiments, the host cell is a yeast cell.

In some embodiments, the yeast cell belongs to the family of Saccharomycetaceae which is a family of yeasts in the order Saccharomycetales that reproduce by budding. In some embodiments, the family of Saccharomycetaceae includes the following genera: *Candida, Kluyveromyces, Komagataella, Kuraishia, Lachancea, Nakaseomyces, Pichia, Saccharomyces, Spathaspora, Tetrapisispora, Zygosaccharomyces* and *Zygotorulaspora.*

In some embodiments, the yeast cell belongs to the genus of *Kluyveromyces.* For example, the yeast cell may be a *Klyveromyces lactis* cell.

In some embodiments, the yeast cell belongs to the genus of *Pichia.* For example, the yeast cell may be a *Pichia pastoris* cell.

In some embodiments, the yeast cell belongs to the genus of *Komagataella.* For example, the yeast cell may be a *Komagataella phaffii* cell, such as a cell of the *Komagataella phaffii* strain ATCC 76273. More information on this strain can be found in the UniProt database (see Taxon Identifier 981350).

In some embodiments, the host cell is not a *Canavalia ensiformis* cell.

In some embodiments, the host cell is a mammalian host cell. Suitable mammalian cells include, but are not limited to, for example, CHO (Chinese Hamster Ovary) cells, BHK cells, HeLa cells, COS cells, HEK-293 and the like. In one embodiment, HEK-293 cells are used. In another embodiment, CHO cells are used.

Step b) of the method of the present invention comprises cultivating the host cell under conditions which allow for the production, i.e. the production of the polypeptide having β-hexosaminidase activity. Such conditions are well-known in the art and, e.g., described in the Examples section.

The method of the present invention may further comprise step c) of obtaining the polypeptide produced in step b). Said polypeptide shall be obtained from the cultivation medium by methods known in the art.

The present invention further relates to a polynucleotide as defined herein above in connection with the method of the present invention, i.e. a polynucleotide encoding a polypeptide having β-hexosaminidase activity and having an amino acid sequence being at least 85% identical to the amino acid sequence shown in SEQ ID NO: 1.

Further encompassed by the present invention is an isolated polypeptide encoded by the polynucleotide of the present invention. The polypeptide has been defined above. The isolated polypeptide may be hexosylated and/or glycosylated.

The present invention further pertains to a host cell comprising the polynucleotide of the present invention, the polypeptide of the present invention and/or the vector of the present invention.

Moreover, the present invention is directed to a vector comprising the polynucleotide of the present invention. In some embodiments, the vector is an expression vector.

The term "vector", typically, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment (e.g., "gene-gun"). Suitable methods for the transformation or transfection of host cells, including yeast cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N Y, 1989) and other laboratory manuals, such as Methods in Molecular Biology, 1995, Vol. 44, Agrobacterium protocols, Ed.: Gartland and Davey, Humana Press, Totowa, New Jersey. Alternatively, a plasmid vector may be introduced by heat shock or electroporation techniques.

In some embodiments, the vector referred to herein is suitable as a cloning vector, i.e. replicable in microbial systems, such as in *E. coli* or in yeast cells.

Further, it is envisaged that the vector of the present invention is an expression vector. In such an expression vector, the polynucleotide comprises an expression cassette as specified above allowing for expression in a host cell. An expression vector may, in addition to the polynucleotide of the invention, also comprise further regulatory elements such as a promoter (e.g. a promoter as described elsewhere herein). Preferably, the expression vector is also a gene transfer or targeting vector.

LIST OF EMBODIMENTS

1. A method of producing a polypeptide having β-hexosaminidase activity, comprising the steps of
   a) providing a yeast cell comprising a polynucleotide encoding a polypeptide having β-hexosaminidase activity and having an amino acid sequence being at least 95% identical to the amino acid sequence shown in SEQ ID NO: 1 or 16,
   b) cultivating said yeast cell under conditions which allow for the production of the polypeptide, and
   c) obtaining the polypeptide produced in step b).
2. The method of embodiment 1, wherein the polypeptide having β-hexosaminidase activity has an amino acid sequence which is at least 98% identical to the amino acid sequence shown in SEQ ID NO: 1.
3. The method of embodiments 1 and 2, wherein the polypeptide having β-hexosaminidase activity comprises an amino acid sequence as shown in SEQ ID NO: 1.
4. The method of embodiments 1 to 3, wherein the yeast cell belongs to the family of Saccharomycetaceae.
5. The method of embodiment 4, wherein the yeast cell is a *Komagataella* cell, such as a *Komagataella phaffii* cell, such as a cell of the *Komagataella phaffii* strain ATCC
6. The method of any one of embodiments 1 to 5, wherein the polynucleotide encoding a polypeptide having β-hexosaminidase activity is operably linked to a heterologous promoter.
7. The method of any one of embodiments 1 to 6, wherein the polynucleotide encoding a polypeptide having β-hexosaminidase activity is codon optimized for the yeast cell.
8. The method of any one of embodiments 1 to 7, wherein the polynucleotide comprises a nucleic acid sequence as shown in SEQ ID NO: 2 or 17.
9. A polynucleotide encoding a polypeptide having β-hexosaminidase activity and having an amino acid sequence being at least 95% identical to the amino acid sequence shown in SEQ ID NO: 1.
10. The polynucleotide of embodiment 9, wherein the polypeptide having β-hexosaminidase activity comprises an amino acid sequence as shown in SEQ ID NO: 1.
11. The polynucleotide of embodiment 9, wherein the polynucleotide is operably linked to a heterologous promoter.
12. A vector, such as an expression vector, comprising the polynucleotide of any one of embodiments 9 to 11.
13. A yeast cell comprising the polynucleotide of any one of embodiments 9 to 11, or the vector of embodiment 12.
14. The yeast cell of embodiment 13, wherein the yeast cell belongs to the family of Saccharomycetaceae.
15. The yeast cell of embodiment 14, wherein the yeast cell is *Komagataella phaffii*.
16. An isolated polypeptide encoded by the polynucleotide of any one of embodiments 9 to 11.

The following examples merely illustrate the invention. They should, whatsoever, not be construed as limiting the scope of protection.

EXAMPLES

Example 1: Introduction

In the studies underlying the present invention, the mRNA sequence and the protein sequence of β-hexosaminidase from *Canavalia ensiformis* were determined. First, the sequence of portions of a β-hexosaminidase protein that has been extracted from *Canavalia ensiformis* plants were determined by preparative digest, MS/MS and N-terminal sequencing. Subsequently, the cDNA sequence was determined by 3' and 5' RACE (Rapid amplification of cDNA ends).

A database research in NCBI and KEGG resulted in the mRNA derived sequences of 4 β-hexosaminidases from *Glycine max* (soybean), the next sequenced relative of *C. ensiformis* (Jack Bean) with the following NCBI IDs:

Chromosome 2 (1668 nt); cDNA XM_003518614.2; protein XP_003518662.1

Chromosome 10 (1632 nt); cDNA XM_003535730.2; protein XP_003535778.1

Chromosome 18 (1698 nt); cDNA XM_003552624.2; protein XP_003552672.1

Chromosome 20 (1641 nt); cDNA XM_003555573.2; protein XP_003555621.1

These sequences served as a basis for primer design and comparison of elucidated sequences.

Example 2: Determination of Portions of the Protein Sequence of a β-Hexosaminidase from *Canavalia ensiformis*

β-hexosaminidase purified from *Canavalia ensiformis* (and having an apparent molecular weight of ~55 kDa) was digested with Lys-C and the resulting peptides were separated via HPLC. After this, Edman degradation was performed with the fractions.

100 µl β-hexosaminidase (~77 µg) were vortexed with 29 mg guanidinium hydrochloride (solid) to reach a final concentration of ~3 M GuaHCl. 7 µl 1.5 M Tris/HCl pH 8.8 were added and shortly vortexed again. 3 µl were taken out for testing the pH on strips (~pH 8.5). The remaining solution was denatured for 20 min at −80° C. and shock cooled in an ice bath.

One vial Lys-C (5 µg, Roche Cat. 11047825001) was reconstituted with 50 µl of water. 5 µl (0.5 µg Lys-C) of this solution were added to the shock cooled solution, vortexed again and incubated at 32° C. for 3 h. 95 µl were directly injected on an Agilent 1200 HPLC equipped with fraction collector using a Waters column (X-Select CSH C18 2.5 µm 2.1×150 mm, Cat. 186006727). Chromatographic separation resulted in sharp peaks with fraction volumes of 100 to 150 µl containing ~25% ACN solvent. 36 fractions were collected (not shown). These were directly used for MALDI-MS to determine the peptide mass (e.g. to estimate the number of Edman cycles).

For some of the obtained fractions the amino acid sequence could be determined by N-terminal Edman sequencing using either an Applied Biosystems Procise HT or Shimadzu PPSQ-33A sequencer under standard conditions. The number of cycles (=amino acid) for each fraction was estimated by a MALDI-MS measurement.

Edman degradation of the fractions resulted in a multitude of sequences that were aligned using ClustalW. In total 208 out of 553 amino acids were identified. The de novo sequenced peptides were superposed to the translated cDNA sequence that was identified as described in Example 3 below (not shown). The results show that the right cDNA sequence was identified in *C. ensiformis.*

Example 3: Determination of the cDNA Sequence of a β-Hexosaminidase from *Canavalia Ensiformis*

Jack Bean (*C. ensiformis*) seeds were put in between wet absorbent tissue into a plastic tray and stored for about 48 hours at a dark place at room temperature (for germination). Afterwards, the germinated seeds were grown for another 5-6 days at light at room temperature. Then the small plants were put into Vermiculite, 3-6 mm as substrate (in 2-3 cm depth) at a sunny window at room temperature and watered if dry.

Germinated material from *C. ensiformis* was cut with a scalpel into parts which can be used for RNA extraction (about 200 mg plant material), put into 50 ml plastic tubes and snap frozen in liquid nitrogen. This was performed with sprout, cotyledon, embryo and leaf tissue. Isolation of RNA from the aforementioned tissues was done according to manufacturer's instructions (RNeasy Plant Mini Kit (Qiagen Cat #74903))

cDNA was synthesized with two reverse transcriptases for sprout, cotyledon, embryo and leaf respectively. Then, cDNAs of both reverse transcriptase reactions for sprout, cotyledon, embryo and leaf respectively were pooled.

Subsequently, an internal fragment of each cDNA was amplified by PCR using Phusion Hot Start II DNA Polymerase (Thermo Scientific, Cat #F-549L) and the following primers:

```
JB-01
                               (SEQ ID NO: 3)
CTCACCTACCTCTGGCCCCTTCCCGC

JB-07
                               (SEQ ID NO: 4)
TTATTGGTCATAACATGACCCTGGACCAACAGG
```

Afterwards, the amplified fragments were subjected to DNA sequence analysis using the Big Dye® Cycle Sequencing Terminator Kit (Applied Biosystems, USA) and the following primers:

```
JB-01
                               (SEQ ID NO: 3)
CTCACCTACCTCTGGCCCCTTCCCGC

JB-02
                               (SEQ ID NO: 5)
GAGGAGCTTCAATTTGGAGTGGATG

JB-06
                               (SEQ ID NO: 6)
ATCAGCTGTCTCACCCCACATGCAAACTTCTC

JB-07
                               (SEQ ID NO: 4)
TTATTGGTCATAACATGACCCTGGACCAACAGG,
```

About 100 ng PCR fragment (or 300 ng plasmid DNA) and 10 pmol primer were amplified with the Big Dye® Cycle Sequencing Terminator Kit, with DyeEX 2.0 Spin Kit purified and sequenced. The Kits and equipment were used according to manufacturer's instructions.

Afterwards, a 3'RACE and 5'RACE were carried out with cDNA obtained from cotyledon tissue.

The following primers were used
For the 3'RACE:

```
JB-08
                               (SEQ ID NO: 7)
AAGTTTGCATGTGGGGTGAGAC

JB-09
                               (SEQ ID NO: 8)
GCAAACAATATGGCCTAGAGCTG

CDSIII-short
                               (SEQ ID NO: 9)
ATTCTAGAGGCCGAGGCGGCCGACATGT
```

Two PCRs, one with JB-08+ CDSIII-short and one with JB-09+ CDSIII-short were performed. PCR fragments were sequenced using the JB-09 primer.

For the 5'RACE:

```
JB-10
                               (SEQ ID NO: 10)
AAGAGTCCTTGGCTTTGGGAAC

Okib57-Adapter
                               (SEQ ID NO: 11)
5'-pGTAGGAATTCGGGTTGTAGGGAGGTCGACATTGCC-3'

JB-01
                               (SEQ ID NO: 3)
CTCACCTACCTCTGGCCCCTTCCCGC

JB-11
                               (SEQ ID NO: 12)
TCAATGTCGCAATGTCATAGGC

JB-12
                               (SEQ ID NO: 13)
ATGAGACTGAACCCAACACTGC

Okib58
                               (SEQ ID NO: 14)
5'-GGCAATGTCGACCTCCCTACAAC-3'

Okib59
                               (SEQ ID NO: 15)
5'-CTCCCTACAACCCGAATTCCTAC-3'
``` cDNA was synthesized with both transcriptases for cotyledon with the specific primer JB-10. Then both cDNAs were pooled. Okib57-Adapter was ligated to the freshly synthesized cDNA. One PCR was performed with primers JB-11 and Okib58 and one PCR was performed with primers JB-12 and Okib59. The resulting fragment was subcloned in PCR-Blunt-II-TOPO and sequenced as described above.

In summary, the mRNA sequence of β-hexosaminidase from *Canavalia ensiformis* was successfully obtained. mRNA could be isolated from different freshly germinated plant material. The corresponding cDNA was sequenced and the found sequence was confirmed by the partial elucidation of the protein sequence of β-hexosaminidase (purified β-hexosaminidase).

Example 4: Recombinant Expression of the Identified Polypeptide

The beta-Hexosaminidase from *Canavalia ensiformis* was recombinantly expressed under control of an AOX1 promoter in *Komagataella phaffii* strain ATCC 76273 (also referred to as CBS 7435). For recombinant expression of beta-Hexosaminidase in 96-deep well plates single colonies were picked from transformation plates into single wells of 96-deep well plates filled with optimized cultivation media. After an initial growth phase to generate biomass, expression from the AOX1 promoter was induced by addition of an optimized liquid mixture allowing for derepressive expression. After a total of 108 hours from the initial inoculation, all deep well plates were centrifuged and supernatants of all wells were harvested into stock microtiter plates for subsequent analysis.

For recombinant expression of beta-Hexosaminidase in fermentation scale, 50 mL of Yeast/Peptone/Glycerol medium in 300 mL shake flask were inoculated with the production strain and shaken at 110 rpm at 28° C. over night (pre-culture 1). Pre-culture 2 (200 mL Yeast/Peptone/Glycerol medium in a 2 L shake flask) was inoculated from pre-culture 1 in that way that the OD600 nm reached approximately 20. Pre-culture 2 was shaken at 220 rpm at 28° C. for about 8 h. 2 L fermenters filled with 400 mL defined medium containing glycerol as carbon source (pH=5.5) were inoculated from pre-culture 2 to an OD600 nm of 2.0, during initial batch phase cultivation temperature was 28° C. One hour prior initiating the production phase temperature was decreased to 24° C. and kept at this level throughout the remaining process, while the pH dropped to 5.0 and was kept at this level. Oxygen saturation was set to 30% throughout the whole process (cascade control: stirrer, flow, oxygen supplementation). Stirring was applied between 700 and 1200 rpm and a flow range (air) of 1.0-2.0 L min-1 was chosen. Glycerol fed-batch was performed by supplying a 60% glycerol solution at 6 g/L h throughout the whole cultivation.

The invention claimed is:

1. A method of producing a polypeptide having β-hexosaminidase activity, comprising the steps of a) providing a yeast cell comprising a polynucleotide encoding a polypeptide having β-hexosaminidase activity and comprising an amino acid sequence that is at least about 95% identical to the amino acid sequence shown in SEQ ID NO: 1 or 16, b) cultivating said yeast cell under conditions which allow for the production of the polypeptide, and c) obtaining the polypeptide produced in step b).

2. The method of claim 1, wherein the polypeptide comprises an amino acid sequence which is at least 98% identical to the amino acid sequence shown in SEQ ID NO: 1.

3. The method of claim 1, wherein the polypeptide comprises the amino acid sequence as shown in SEQ ID NO: 1.

4. The method of claim 1, wherein the yeast cell belongs to the family of Saccharomycesaceae.

5. The method of claim 1, wherein the yeast cell is a *Komagataella* cell.

6. The method of claim 1, wherein the polynucleotide is operably linked to a heterologous promoter.

7. The method of claim 1, wherein the polynucleotide is codon optimized for the yeast cell.

8. The method of claim 1, wherein the polynucleotide comprises the nucleic acid sequence as shown in SEQ ID NO: 2 or 17.

9. The method of claim 3, wherein the yeast cell belongs to the family of Saccharomycesaceae.

10. The method of claim 3, wherein the yeast cell is a *Komagataella* cell.

11. The method of claim 10, wherein the *Komagataella* cell is a *Komagataella phaffii* cell.

12. The method of claim 5, wherein the *Komagataella* cell is a *Komagataella phaffii* cell.

* * * * *

SEQUENCE LISTING

```
<160> NUMBER OF SEQ ID NOS: 18

<210> SEQ ID NO 1
<211> LENGTH: 523
<212> TYPE: PRT
<213> ORGANISM: Canavalia ensiformis

<400> SEQUENCE: 1

Ala Thr Leu Lys Ser Ile Ile Glu Pro Thr Glu Ser Leu Thr Tyr Leu
1               5                   10                  15

Trp Pro Leu Pro Ala Asp Phe Thr Ser Gly Asp Glu Thr Leu Ser Val
            20                  25                  30

Asp Pro Ala Leu Thr Leu Ser Val Ala Gly Asn Gly Gly Gly Ser Ser
        35                  40                  45

Ile Leu Arg Asp Ala Phe Asp Arg Tyr Arg Gly Ile Ile Phe Lys His
    50                  55                  60

Ser Ser Val Gly Phe Ser Leu Ile Arg Lys Leu Arg Glu Arg Leu Val
65                  70                  75                  80

Ser Val Ser Ala Tyr Asp Ile Ala Thr Leu Lys Ile Thr Val His Ser
                85                  90                  95

Asp Asn Glu Glu Leu Gln Leu Gly Val Asp Glu Thr Tyr Thr Leu Leu
            100                 105                 110

Val Pro Lys Ala Lys Asp Ser Tyr Val Ala Gly Glu Val Thr Ile Glu
        115                 120                 125

Ala Asn Thr Val Tyr Gly Ala Leu Arg Gly Leu Glu Thr Phe Ser Gln
    130                 135                 140

Leu Cys Ser Phe Asp Tyr Ser Asp Lys Thr Ile Lys Ile Tyr Lys Ala
145                 150                 155                 160

Pro Trp Ser Ile Gln Asp Lys Pro Arg Phe Ser Tyr Arg Gly Leu Leu
                165                 170                 175

Leu Asp Thr Ser Arg His Tyr Leu Pro Ile Asn Val Ile Lys Gln Ile
            180                 185                 190

Ile Glu Ser Met Ser Tyr Ala Lys Leu Asn Val Leu His Trp His Ile
        195                 200                 205

Ile Asp Glu Glu Ser Phe Pro Leu Glu Val Pro Thr Tyr Pro Asn Leu
    210                 215                 220

Trp Lys Gly Ser Tyr Thr Lys Trp Glu Arg Tyr Thr Val Glu Asp Ala
225                 230                 235                 240

Tyr Glu Ile Val Asn Phe Ala Lys Met Arg Gly Ile Asn Val Met Ala
                245                 250                 255
```

```
Glu Val Asp Val Pro Gly His Ala Glu Ser Trp Gly Ala Gly Tyr Pro
            260                 265                 270

Asn Leu Trp Pro Ser Pro Ser Cys Arg Glu Pro Leu Asp Val Ser Lys
            275                 280                 285

Asn Phe Thr Phe Asp Val Ile Ser Gly Ile Leu Thr Asp Ile Arg Lys
            290                 295                 300

Ile Phe Pro Phe Glu Leu Phe His Leu Gly Gly Asp Glu Val Asn Thr
305                 310                 315                 320

Asp Cys Trp Thr Ser Thr Ser His Val Lys Glu Trp Leu Ser Thr Gln
                325                 330                 335

Asn Met Thr Ala Lys Asp Ala Tyr Glu Tyr Phe Val Leu Lys Ala Gln
            340                 345                 350

Glu Ile Ala Val Ser Lys Asn Trp Ser Pro Val Asn Trp Glu Glu Thr
            355                 360                 365

Phe Asn Thr Phe Pro Ala Lys Leu His Lys Lys Thr Val Val His Asn
            370                 375                 380

Trp Leu Gly Pro Gly Val Cys Pro Lys Val Val Ala Lys Gly Phe Arg
385                 390                 395                 400

Cys Ile Phe Ser Asn Gln Gly Val Trp Tyr Leu Asp His Leu Asp Val
                405                 410                 415

Pro Trp Asp Glu Val Tyr Thr Ala Glu Pro Leu Glu Gly Ile Glu Lys
            420                 425                 430

Ser Ser Glu Gln Glu Leu Val Ile Gly Gly Glu Val Cys Met Trp Gly
            435                 440                 445

Glu Thr Ala Asp Thr Ser Asn Val Gln Gln Thr Ile Trp Pro Arg Ala
            450                 455                 460

Ala Ala Ala Ala Glu Arg Leu Trp Ser Gln Arg Asp Ser Thr Asn Ile
465                 470                 475                 480

Thr Val Thr Ala Leu Pro Arg Leu Gln Asn Phe Arg Cys Leu Leu Asn
                485                 490                 495

Lys Arg Gly Val Ala Ala Ala Pro Val Lys Asn Tyr Tyr Ala Arg Arg
                500                 505                 510

Ala Pro Ser Gly Pro Gly Ser Cys Tyr Glu Gln
            515                 520
```

<210> SEQ ID NO 2
<211> LENGTH: 1569
<212> TYPE: DNA
<213> ORGANISM: Canavalia ensiformis

<400> SEQUENCE: 2

```
gctactttga agtccatcat cgagccaact gagtccttga cttacttgtg gccattgcca        60
gctgacttca cttctggtga cgaaactttg tctgttgacc cagctttgac tttgtccgtt       120
gctggtaatg gtggtggttc ctccattttg agagatgctt cgacagata cagaggtatt       180 atcttcaagc actcctccgt tggattctct ttgatcagaa agttgagaga gagattggtt       240
tccgtttccg cttacgacat tgctactttg aagatcactg ttcactccga caacgaagag       300
ttgcagttgg gtgttgacga gacttacact ttgttggttc aaaaggctaa ggactcctac       360
gttgctggtg aggttactat cgaggctaac actgtttacg gtgctttgag aggtttggag       420
actttctccc agttgtgttc cttcgactac tctgacaaga ctatcaagat ttacaaggct       480
ccttggtcca tccaggacaa gccaagattt tcctacagag gtttgttgtt ggacacttcc       540
agacactact tgccaatcaa cgttatcaag cagatcatcg agtccatgtc ctacgctaag       600
```

-continued

```
ttgaacgttt tgcactggca catcatcgac gaagagtctt tcccattgga ggttccaact    660
tacccaaact tgtggaaggg ttcctacact aagtgggaga gatacactgt tgaggacgct    720
tacgagatcg ttaacttcgc taagatgaga ggtattaacg ttatggctga ggttgacgtt    780
ccaggtcatg ctgaatcttg gggtgctggt tatccaaatt tgtggccatc tccatcctgt    840
agagagccat tggacgtttc caagaacttc actttcgacg ttatctccgg aatcttgact    900
gacatcagaa agatattccc attcgagttg ttccacttgg gaggtgacga ggttaatact    960
gactgttgga cttccacttc ccacgttaag gaatggttgt ccactcagaa catgactgct   1020
aaggatgctt acgaatactt cgttttgaag gctcaagaga tcgctgtttc taagaactgg   1080
tcccctgtta actgggaaga gactttcaac actttcccag ctaagttgca caagaaaact   1140
gttgttcaca actggttggg tccaggtgtt tgtccaaagg ttgttgctaa gggtttcaga   1200
tgtatcttct ccaaccaggg tgtttggtac ttggaccact tggatgttcc ttgggacgag   1260
gtttacactg ctgaaccatt ggaaggtatc gagaagtcct ctgagcaaga gttggttatc   1320
ggtggtgaag tttgtatgtg gggtgagact gctgacactt ctaacgttca gcagactatc   1380
tggccaagag ccgcagctgc tgctgaaaga ttgtggtccc aaagagactc cactaacatc   1440
actgttactg ctttgccaag attgcagaac ttcagatgtt tgttgaacaa gagaggtgtt   1500
gctgctgctc cagttaagaa ctactacgct agaagagccc catccggtcc aggttcttgt   1560
tacgaacaa                                                          1569

<210> SEQ ID NO 3
<211> LENGTH: 26
<212> TYPE: DNA
<213> ORGANISM: Artificial Sequence
<220> FEATURE:
<223> OTHER INFORMATION: Primer JB-01

<400> SEQUENCE: 3
ctcacctacc tctggcccct tcccgc                                          26

<210> SEQ ID NO 4
<211> LENGTH: 33
<212> TYPE: DNA
<213> ORGANISM: Artificial Sequence
<220> FEATURE:
<223> OTHER INFORMATION: Primer JB-07

<400> SEQUENCE: 4
ttattggtca taacatgacc ctggaccaac agg                                  33

<210> SEQ ID NO 5
<211> LENGTH: 25
<212> TYPE: DNA
<213> ORGANISM: Artificial Sequence
<220> FEATURE:
<223> OTHER INFORMATION: Primer JB-02

<400> SEQUENCE: 5
gaggagcttc aatttggagt ggatg                                           25

<210> SEQ ID NO 6
<211> LENGTH: 32
<212> TYPE: DNA
<213> ORGANISM: Artificial Sequence
<220> FEATURE:
<223> OTHER INFORMATION: Primer JB-06

<400> SEQUENCE: 6
```

-continued

```
atcagctgtc tcaccccaca tgcaaacttc tc                          32

<210> SEQ ID NO 7
<211> LENGTH: 22
<212> TYPE: DNA
<213> ORGANISM: Artificial Sequence
<220> FEATURE:
<223> OTHER INFORMATION: Primber JB-08

<400> SEQUENCE: 7
aagtttgcat gtggggtgag ac                                     22

<210> SEQ ID NO 8
<211> LENGTH: 23
<212> TYPE: DNA
<213> ORGANISM: Artificial Sequence
<220> FEATURE:
<223> OTHER INFORMATION: Primer JB-09

<400> SEQUENCE: 8
gcaaacaata tggcctagag ctg                                    23

<210> SEQ ID NO 9
<211> LENGTH: 28
<212> TYPE: DNA
<213> ORGANISM: Artificial Sequence
<220> FEATURE:
<223> OTHER INFORMATION: CDSIII-short

<400> SEQUENCE: 9
attctagagg ccgaggcggc cgacatgt                               28

<210> SEQ ID NO 10
<211> LENGTH: 22
<212> TYPE: DNA
<213> ORGANISM: Artificial Sequence
<220> FEATURE:
<223> OTHER INFORMATION: JB-10

<400> SEQUENCE: 10
aagagtcctt ggctttggga ac                                     22

<210> SEQ ID NO 11
<211> LENGTH: 35
<212> TYPE: DNA
<213> ORGANISM: Artificial Sequence
<220> FEATURE:
<223> OTHER INFORMATION: Okib57-Adapter

<400> SEQUENCE: 11
gtaggaattc gggttgtagg gaggtcgaca ttgcc                       35

<210> SEQ ID NO 12
<211> LENGTH: 22
<212> TYPE: DNA
<213> ORGANISM: Artificial Sequence
<220> FEATURE:
<223> OTHER INFORMATION: JB-11

<400> SEQUENCE: 12
tcaatgtcgc aatgtcatag gc                                     22

<210> SEQ ID NO 13
<211> LENGTH: 22
<212> TYPE: DNA
```

-continued

US 12,630,810 B2

```
<213> ORGANISM: Artificial Sequence
<220> FEATURE:
<223> OTHER INFORMATION: JB-12

<400> SEQUENCE: 13
atgagactga acccaacact gc                                                 22

<210> SEQ ID NO 14
<211> LENGTH: 23
<212> TYPE: DNA
<213> ORGANISM: Artificial Sequence
<220> FEATURE:
<223> OTHER INFORMATION: Okib58

<400> SEQUENCE: 14
ggcaatgtcg acctccctac aac                                                23

<210> SEQ ID NO 15
<211> LENGTH: 23
<212> TYPE: DNA
<213> ORGANISM: Artificial Sequence
<220> FEATURE:
<223> OTHER INFORMATION: Okib59

<400> SEQUENCE: 15
ctccctacaa cccgaattcc tac                                                23

<210> SEQ ID NO 16
<211> LENGTH: 553
<212> TYPE: PRT
<213> ORGANISM: Canavalia ensiformis

<400> SEQUENCE: 16

Met Phe Leu Cys Ile Pro Arg Trp Phe Ser Ser Pro Leu Leu Ile Leu
1               5                   10                  15

Phe Val Ile Tyr Cys Ala Leu Phe Ala Pro Gln Ala Ala Ser Ala Thr
                20                  25                  30

Leu Lys Ser Ile Ile Glu Pro Thr Glu Ser Leu Thr Tyr Leu Trp Pro
            35                  40                  45

Leu Pro Ala Asp Phe Thr Ser Gly Asp Glu Thr Leu Ser Val Asp Pro
        50                  55                  60

Ala Leu Thr Leu Ser Val Ala Gly Asn Gly Gly Gly Ser Ser Ile Leu
65                  70                  75                  80

Arg Asp Ala Phe Asp Arg Tyr Arg Gly Ile Ile Phe Lys His Ser Ser
                85                  90                  95

Val Gly Phe Ser Leu Ile Arg Lys Leu Arg Glu Arg Leu Val Ser Val
                100                 105                 110

Ser Ala Tyr Asp Ile Ala Thr Leu Lys Ile Thr Val His Ser Asp Asn
            115                 120                 125

Glu Glu Leu Gln Leu Gly Val Asp Glu Thr Tyr Thr Leu Leu Val Pro
        130                 135                 140

Lys Ala Lys Asp Ser Tyr Val Ala Gly Glu Val Thr Ile Glu Ala Asn
145                 150                 155                 160

Thr Val Tyr Gly Ala Leu Arg Gly Leu Glu Thr Phe Ser Gln Leu Cys
                165                 170                 175

Ser Phe Asp Tyr Ser Asp Lys Thr Ile Lys Ile Tyr Lys Ala Pro Trp
            180                 185                 190

Ser Ile Gln Asp Lys Pro Arg Phe Ser Tyr Arg Gly Leu Leu Leu Asp
            195                 200                 205
```

```
Thr Ser Arg His Tyr Leu Pro Ile Asn Val Ile Lys Gln Ile Ile Glu
    210                 215                 220

Ser Met Ser Tyr Ala Lys Leu Asn Val Leu His Trp His Ile Ile Asp
225                 230                 235                 240

Glu Glu Ser Phe Pro Leu Glu Val Pro Thr Tyr Pro Asn Leu Trp Lys
                245                 250                 255

Gly Ser Tyr Thr Lys Trp Glu Arg Tyr Thr Val Glu Asp Ala Tyr Glu
                260                 265                 270

Ile Val Asn Phe Ala Lys Met Arg Gly Ile Asn Val Met Ala Glu Val
                275                 280                 285

Asp Val Pro Gly His Ala Glu Ser Trp Gly Ala Gly Tyr Pro Asn Leu
    290                 295                 300

Trp Pro Ser Pro Ser Cys Arg Glu Pro Leu Asp Val Ser Lys Asn Phe
305                 310                 315                 320

Thr Phe Asp Val Ile Ser Gly Ile Leu Thr Asp Ile Arg Lys Ile Phe
                325                 330                 335

Pro Phe Glu Leu Phe His Leu Gly Gly Asp Glu Val Asn Thr Asp Cys
                340                 345                 350

Trp Thr Ser Thr Ser His Val Lys Glu Trp Leu Ser Thr Gln Asn Met
                355                 360                 365

Thr Ala Lys Asp Ala Tyr Glu Tyr Phe Val Leu Lys Ala Gln Glu Ile
    370                 375                 380

Ala Val Ser Lys Asn Trp Ser Pro Val Asn Trp Glu Glu Thr Phe Asn
385                 390                 395                 400

Thr Phe Pro Ala Lys Leu His Lys Lys Thr Val Val His Asn Trp Leu
                405                 410                 415

Gly Pro Gly Val Cys Pro Lys Val Val Ala Lys Gly Phe Arg Cys Ile
                420                 425                 430

Phe Ser Asn Gln Gly Val Trp Tyr Leu Asp His Leu Asp Val Pro Trp
                435                 440                 445

Asp Glu Val Tyr Thr Ala Glu Pro Leu Glu Gly Ile Glu Lys Ser Ser
    450                 455                 460

Glu Gln Glu Leu Val Ile Gly Gly Glu Val Cys Met Trp Gly Glu Thr
465                 470                 475                 480

Ala Asp Thr Ser Asn Val Gln Gln Thr Ile Trp Pro Arg Ala Ala Ala
                485                 490                 495

Ala Ala Glu Arg Leu Trp Ser Gln Arg Asp Ser Thr Asn Ile Thr Val
                500                 505                 510

Thr Ala Leu Pro Arg Leu Gln Asn Phe Arg Cys Leu Leu Asn Lys Arg
                515                 520                 525

Gly Val Ala Ala Ala Pro Val Lys Asn Tyr Tyr Ala Arg Arg Ala Pro
    530                 535                 540

Ser Gly Pro Gly Ser Cys Tyr Glu Gln
545                 550
```

```
<210> SEQ ID NO 17
<211> LENGTH: 1662
<212> TYPE: DNA
<213> ORGANISM: Canavalia ensiformis

<400> SEQUENCE: 17
atgtttctgt gcatacccag atggttctct tcacctcttc tcattctctt tgtcatttac      60
tgtgccctct ttgctcctca agctgcttct gccacactca aatctatcat tgaacccact     120
gagtccctca catacctttg gcccctcccc gcagacttca cttcaggcga tgaaactctt     180
```

```
tccgttgacc ctgcacttac cctctctgtc gccggcaacg gtggtggctc ttccattctc        240
agagatgcat ttgaccgata cagaggaatc atattcaagc acagcagtgt tgggttcagt        300
ctcataagaa agttaaggga aagattggtg tctgtttctg cctatgacat tgcgacattg        360
aagatcactg tccattcaga taacgaggag cttcaacttg gagtggatga aacctatacc        420
ttgctggttc ccaaagccaa ggactcttat gttgctgggg aagtcacaat tgaggcaaac        480
actgtttatg gtgcattgcg cggattagag acattcagcc agttgtgttc tttcgattat        540
tcggataaaa caataaaaat atacaaggca ccttggtcca tccaagataa acctagattt        600
tcctatcgtg ggctttttgtt ggacacatcg aggcactatt taccaattaa cgtaattaag        660
cagattattg aatctatgtc ctatgctaaa cttaatgttc tacattggca catcatagac        720
gaggagtcat ttcctcttga ggtacctaca tatccaaact tgtggaaagg ttcatataca        780
aagtgggaac gttacacggt agaagacgca tatgaaattg tcaacttcgc caaaatgaga        840
ggcataaatg tgatggcaga agtggatgtt cctggtcatg cagaatcatg gggtgctgga        900
tatcccaatc tttggccgtc accttcctgt agggagccac tggatgtttc aaagaatttt        960
acttttgatg tcatttctgg tatcctgaca gatataagaa agattttccc gtttgagcta       1020
tttcacttgg gtggtgatga agttaataca gattgctgga ccagtacttc tcatgtgaag       1080
gaatggcttt cgactcaaaa catgactgct aaagatgcct atgaatattt tgtactgaag       1140
gcccaagaga tagctgtttc aaaaaattgg agtccggtga actgggaaga aaccttcaat       1200
acatttccag caaagctcca taagaaaact gtggtgcata actggttggg ccctgggggtt       1260 tgtccaaagg ttgttgcaaa aggtttcagg tgcattttca gtaatcaggg tgtctggtat       1320
cttgaccatc tggatgtacc ttgggatgag gtctatactg ctgagccact agaaggaata       1380
gaaaaatctt ctgaacaaga gcttgtaatt ggaggagaag tttgcatgtg gggtgagaca       1440
gctgatacat ccaatgttca gcaaacaata tggcctagag ctgctgcagc tgcagaacgc       1500
ttatggagtc agagagattc tacaaatatt actgtaactg cgttgccccg gttacaaaac       1560
ttcagatgtc tattgaataa acgtggagtt gcagctgctc ctgtgaaaaa ttattatgct       1620
agaagggctc ctagtggtcc aggctcatgt tatgagcaat aa                          1662
```

<210> SEQ ID NO 18
<211> LENGTH: 1572
<212> TYPE: DNA
<213> ORGANISM: Artificial Sequence
<220> FEATURE:
<223> OTHER INFORMATION: codon optimized sequence (for human cells)

<400> SEQUENCE: 18

```
gccacactga agtccatcat cgagcccacc gagagcctga cctacctgtg gcctctgccc         60
gccgatttca ccagcggcga cgagacactg tccgtggatc ctgccctgac actgagcgtg        120 gccgaaatg gcggcggaag cagcatcctg agagatgcct cgaccggta cagaggcatc        180 atcttcaagc acagcagcgt gggcttcagc ctgatccgga agctgcgcga gagactggtg        240
tccgtgtccg cctacgatat cgccacacctg aagatcaccg tgcactccga caacgaggaa        300
ctgcagctgg gcgtggacga cgatacaccc ctgctggtgc ccaaggccaa ggacagctat        360
gtggccggcg aagtgaccat cgaggccaac acagtgtacg gcgccctgag aggcctggaa        420
accttcagcc agctgtgcag cttcgactac agcgacaaga ccatcaagat ctacaaggcc        480
ccttggagca tccaggacaa gccccggttc agctacagag gcctgctgct ggacaccagc        540
```

-continued

```
agacactacc tgcccatcaa cgtgatcaag cagatcatcg agagcatgag ctacgccaag    600
ctgaacgtgc tgcactggca catcatcgac gaggaatcct tcccactgga agtgcccacc    660
taccccaacc tgtggaaggg cagctacacc aagtgggagc ggtacaccgt ggaagatgcc    720
tacgagatcg tgaacttcgc caagatgcgg ggcatcaatg tgatggccga ggtggacgtg    780
ccaggccacg ctgaatcttg gggagccggc taccctaatc tgtggcccag ccccagctgt    840
cgcgaacccc tggacgtgtc caagaacttc accttcgacg tgatcagcgg catcctgacc    900
gatatcagaa agatcttccc attcgagctg ttccacctgg gaggcgacga agtgaacacc    960
gactgctgga ccagcaccag ccacgtgaaa gagtggctga gcacccagaa catgaccgcc   1020
aaggacgcct acgagtactt cgtgctgaag gcccaggaaa tcgccgtgtc taagaattgg   1080
agccccgtga actgggagga aacctttaac accttccctg ccaaactgca caagaaaacc   1140
gtggtgcaca attggctggg ccctggcgtg tgccctaagg tggtggccaa gggcttccgc   1200
tgcatattca gcaaccaggg cgtgtggtat ctggaccacc tggatgtgcc ctgggacgag   1260
gtgtacacag ccgagcctct ggaaggcatc gagaagtcct ccgagcagga actcgtgatc   1320
ggcggagaag tgtgcatgtg gggcgagaca gccgacacct ccaacgtgca gcagaccatc   1380
tggcctagag ccgccgctgc cgctgaaaga ctgtggtccc agagagacag caccaacatc   1440
accgtgaccg ccctgccccg gctgcagaac tttagatgcc tgctgaacaa gcggggcgtg   1500
gccgctgccc ccgtgaagaa ttactatgcc agaagggccc ccagcggccc tggcagctgt   1560
tatgaacagt ga                                                       1572
```